US011385242B2

(12) United States Patent
Shinitzky et al.

(10) Patent No.: US 11,385,242 B2
(45) Date of Patent: Jul. 12, 2022

(54) PEPTIDE COMBINATIONS FOR USE IN THE DIAGNOSIS OF SCHIZOPHRENIA

(71) Applicant: YEDA RESEARCH AND DEVELOPMENT CO. LTD., Rehovot (IL)

(72) Inventors: Meir Shinitzky, Rehovot (IL); Ludmila Schechtman, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 0 days.

(21) Appl. No.: 15/744,532

(22) PCT Filed: Jul. 14, 2016

(86) PCT No.: PCT/IL2016/050768
§ 371 (c)(1),
(2) Date: Aug. 9, 2018

(87) PCT Pub. No.: WO2017/009846
PCT Pub. Date: Jan. 19, 2017

(65) Prior Publication Data
US 2018/0348234 A1 Dec. 6, 2018

Related U.S. Application Data

(60) Provisional application No. 62/192,206, filed on Jul. 14, 2015.

(51) Int. Cl.
G01N 33/68 (2006.01)
C07K 14/47 (2006.01)
C07K 7/04 (2006.01)

(52) U.S. Cl.
CPC ........... G01N 33/6896 (2013.01); C07K 7/04 (2013.01); C07K 14/4713 (2013.01); G01N 2800/302 (2013.01)

(58) Field of Classification Search
None
See application file for complete search history.

(56) References Cited

U.S. PATENT DOCUMENTS

| 2002/0010319 A1* | 1/2002 | Ansaldi | C07K 16/4291 530/387.1 |
| 2005/0089927 A1* | 4/2005 | Deckmann | C07K 14/4713 435/7.1 |
| 2012/0259092 A1 | 10/2012 | Chatenet et al. | |

FOREIGN PATENT DOCUMENTS

| EP | 1 584 627 A1 | 10/2005 |
| KR | 10-2013-0057012 A | 5/2013 |
| WO | 99/30163 A1 | 6/1999 |
| WO | 99/51725 A2 | 10/1999 |
| WO | 92/074793 A2 | 9/2002 |
| WO | 2011/085110 A1 | 7/2011 |
| WO | 2015/019979 A1 | 2/2015 |

OTHER PUBLICATIONS

Kumagai "Structural Consequences of Target Epitope-directed Functional Alteration of an Antibody" JBC 278(27):24929-24936 (Year: 2003).*
Steers "Designing the epitope flanking regions for optimal generationof CTL epitopes" vaccine 32:3509-3516 (Year: 2014).*
Ladner "mapping the epitopes of antibodies" biotech gen engin review 24:1-30 (Year: 2007).*
Shinitzky et al., "Platelet autoantibodies in dementia and schizophrenia. Possible implication for mental disorders", Ann N Y Acad Sci., vol. 621, pp. 205-217, (1991).
Deckmann et al., "Humoral and cellular response against autologous platelets in schizophrenia. Clinical and pathophysiological implications", Ital J Psych Behav Sci, vol. 6, pp. 29-34, (1996).
Ebert et al., "Effect of Clozapine and Other Antipsychotics on the Level of Platelet-Associated Autoantibodies in Children with Schizophrenia: A Longitudinal Follow-Up Study", Neuropsychobiology, vol. 71, No. 2, pp. 120-124, (2015).
NIH Policy and Guidelines on the Inclusion of Children as Participants in Research Involving Human Subjects. Mar. 6, 1998. Link: http://grants.nih.gov/grants/guide/notice-files/not98-024.html. See also change in this policy, dated Oct. 13, 2015. Link: http://grants.nih.gov/grants/guide/notice-files/NOT-OD-16-010.html.
Song et el. "Design of an Acid-Activated Antimicrobial Peptide for Tumor Therapy", Mol. Pharmaceutics, vol. 10, No. 5, pp. 2934-2941, (2013).
Krajewski et al. "Design and Synthesis of Dimeric HIV-1 Integrase Inhibitory Peptides", Bioorganic & Medicinal Chemistry Letters, vol. 13, No. 19, pp. 3203-3205, (2003).
Abramsky et al., "Autoimmune response to dopamine-receptor as a possible mechanism in the pathogenesis of Parkinson's disease and schizophrenia", Perspect Biol Med., 1978, vol. 22, No. 1, pp. 104-114. Abstract only.
Asor et al., "Platelets: A possible glance into brain biological processes in schizophrenia", World Journal of Psychiatry, 2012, vol. 2, No. 6, pp. 124-133.
Burbaeva et al., "Concentration of neuron- and non-neuron-specific enolase isoenzymes in different structures of the brains of mentally healthy subjects and schizophrenic patients", Zh Nevropatol Psikhiatr Im S S Korsakova, 1987, vol. 87, No. 1, pp. 104-109. Abstract only.
Deckmann et al., "A conformational epitope which detects autoantibodies from schizophrenic patients", Clinica Chimica Acta, 2002, vol. 322, pp. 91-98.
Ebert et al., "High Circulatory Titer of Platelet-Associated Autoantibodies in Childhood Onset Schizophrenia and its Diagnostic Implications", Neuropsychobiology, 2013, vol. 68, pp. 124-127.

(Continued)

Primary Examiner — Adam Weidner
(74) Attorney, Agent, or Firm — Vorys, Sater, Seymour and Pease LLP; Anthony Venturino

(57) ABSTRACT

Provided is a composition including a combination of at least one short peptide and at least one peptide dimer, in defined ratio, to which autoantibodies found in elevated levels in schizophrenic patients bind.

10 Claims, No Drawings
Specification includes a Sequence Listing.

(56) References Cited

OTHER PUBLICATIONS

Kessler et al., "Platelets from schizophrenic patients bear autoimmune antibodies that inhibit dopamine uptake", Psychobiology, 1993, vol. 21, No. 4, pp. 299-306.

Kessler et al., "Number of platelet dense granules varies with age, schizophrenia and dementia", Dementia, 1995, vol. 6, No. 6, pp. 330-333. Abstract only.

Levine et al., "Treatment of schizophrenia with an immunosuppresant", The Lancet, 1994, vol. 344, No. 8914, pp. 59-60.

Levine et al., "Side Effect Profile of Azathioprine in the Treatment of Chronic Schizophrenic Patients", Neuropsychobiology, 1997, vol. 36, pp. 172-176.

Leykin et al., "Short and long term immunosuppresive effects of clozapine and haloperidol", Immunopharmacology, 1997, vol. 37, pp. 75-86.

Leykin et al., "Elevated Cellular Immune Response to Human Heat-Shock Protein-60 in Schizophrenic Patients", Eur Arch Psychiatry Clin Nurosci, 1999, vol. 249, pp. 238-246.

Marangos et al., "Blood Platelets Contain a Neuron-Specific Enolase Subunit", Journal of Neurochemistry, 1980, vol. 34, No. 5, pp. 1254-1258.

Muller et al.,"The role of inflammation in schizophrenia", Frontiers in Neuroscience, 2015, vol. 9, Article 372, pp. 1-9.

Muller, "Inflammation in Schizophrenia: Pathogenetic Aspects and Therapeutic Considerations", Schizophr Bull., 2018, vol. 44, No. 5, pp. 973 982. Abstract only.

Pandarakalam, "The Autoimmune and Infectious Etiological Factors of a Subset of Schizophrenia", British Journal of Medical Practitioners, 2015, vol. 8, No. 4, pp. a831, 1-10.

Pollak et al., "Antibodies in the Diagnosis, Prognosis, and Prediction of Psychotic Disorders", Schizophrenia Bulletin, 2018, pp. 1-14.

Schwarz et al., "Blood-cerebrospinal fluid barrier impairment as indicator for an immune in schizophrenia", Neuroscience Letters, 1998, vol. 253, No. 3, pp. 201-203.

Shinitzky et al., "Autoimmunity Against Platelets in Schizophrenia", The Decade of Autoimmunity, 1999, Elsevier Science B.V., Ed. Y. Shoenfeld, pp. 277-284.

Spivak et al., "Blind Verification of Elevated Platelet Autoantibodies in Serum of Schizophrenic Patients—Part I: Young Subjects", Neuropsychobiology, 2009, vol. 60, No. 1, pp. 44-48.

Spivak et al., "Blind Verification of Elevated Platelet Autoantibodies in Serum of Schizophrenic Patients—Part II: Adult Subjects", Neuropsychobiology, 2009, vol. 60 No. 1, pp. 49-54.

Vermuyten et al., "Detection of neuron specific enolase concentrations in cerebrospinal fluid from patients with neurological disorders by means of a sensitive enzyme immunoassay", Clinica Chimica Acta, 1990, vol. 187, No. 2, pp. 69-78.

* cited by examiner

PEPTIDE COMBINATIONS FOR USE IN THE DIAGNOSIS OF SCHIZOPHRENIA

SEQUENCE LISTING

The Sequence Listing submitted in text format (.txt) filed on Jan. 12, 2018, named "SequenceListing.txt", created on Jul. 14, 2016, 5.07 KB), is incorporated herein by reference.

TECHNOLOGICAL FIELD

The invention generally concerns novel peptide combinations for the diagnosis of Schizophrenia.

BACKGROUND ART

Schizophrenia is a syndrome which encompasses a variety of mental symptoms like auditory hallucinations, paranoia, delusions, catatonia, bizarre behavior and emotional withdrawal. Schizophrenia affects about 1% of the total population and its economical as well as social burdens on society are enormous. The onset of the disease occurs in early age and, thus, patients typically need life-long medical and psychiatric supervision. Schizophrenia is, therefore, rated as one of the most costly diseases in the industrial world.

Schizophrenia has been shown to involve an autoimmune process and lately autoantibodies and cytotoxic T-cells against platelets were demonstrated in schizophrenic patients. The cytotoxic T-cell reaction in schizophrenic patients was evaluated by a skin test in which most schizophrenic patients reacted positively against their autologous platelets whereas only a very minor number of non-schizophrenic tested individuals reacted positively in this test [1].

In addition, elevated levels of autoantibodies against platelets were observed in schizophrenic patients but not in patients suffering from manic-depressive disorder, depression, personality disorders and schizoaffective disorder [2, 3].

Previous studies demonstrated several proteins which bind autoantibodies that are found in elevated levels in body fluids of schizophrenic patients [4]. These proteins reacted with purified platelet-derived autoantibodies (PAA) from schizophrenic patients but could not differentiate between plasma or blood samples of schizophrenic and non-schizophrenic individuals. Enzymatic digestion of one of these proteins, the enzyme Enolase, resulted in a fragment which bound substantially higher to plasma samples of schizophrenic patients compared to plasma samples of non-schizophrenic individuals. On the basis of this fragment several additional peptides were synthesized and such having a high binding activity to PAAs of schizophrenic individuals were isolated. These synthesized peptides are each comprised of at least 7 amino acids.

The Effect of clozapine and other antipsychotics on the level of PAAs in children with schizophrenia was also studied [5].

REFERENCES

[1] WO99/30163
[2] Shinitzky M, Deckmann M, Kessler A, Sirota P, Rabbs A, Elizur A. Platelet autoantibodies in dementia and schizophrenia. Possible implication for mental disorders. *Ann N Y Acad Sci.* 1991; 621:205-17.
[3] Deckmann M, Shinitzky M, Leykin I, Cheng D, Guy J, Sirota P, et al. Humoral and cellular response against autologous platelets in schizophrenia-clinical and pathophysiological implications. *Ital J Psych Behav Sci,* 1996; 6:29-34.
[4] WO99/51725
[5] Ebert T, Schechtman M, Midbari Y, Weizman A, Shinitzky M, Spivak B. Effect of Clozapine and Other Antipsychotics on the Level of Platelet-Associated Autoantibodies in Children with Schizophrenia: A Longitudinal Follow-Up Study. *Neuropsychobiology.* 2015 Apr. 9; 71(2):120-124.
[6] WO02/074793
[7] NIH POLICY AND GUIDELINES ON THE INCLUSION OF CHILDREN AS PARTICIPANTS IN RESEARCH INVOLVING HUMAN SUBJECTS. Mar. 6, 1998. Link: grants dot nih dot gov forward slash grants forward slash guide forward slash notice-files forward slash not98-024 dot html. See also change in this policy, dated Oct. 13, 2015. Link: grants dot nih dot gov forward slash grants forward slash guide forward slash notice-files forward slash NOT-OD-16-010 dot html.

GENERAL DESCRIPTION

The present invention provides a composition comprising a combination of at least one short peptide and at least one peptide dimer, in defined ratio, to which autoantibodies found in elevated levels in schizophrenic patients bind. The particular combinations enable autoantibodies to bind to the peptide-based materials, thereby rendering the compositions of the invention most useful in the diagnosis of schizophrenia. Thus, although peptides of the prior art [4,6] were able to bind to autoantibodies present at higher levels in schizophrenic patients as compared to non-schizophrenic individuals, the peptide combinations of the present invention demonstrate a vastly improved affinity and unique characteristics which enable a more efficient and early detection of schizophrenia in children (i.e. under the age of 18, as per NIH policy [7] and young adults, being 18-19 years old).

As demonstrated herein, assays of the art exhibited a sensitivity which is at best about 20%, while the combination of the present invention demonstrated a sensitivity of about 80%.

Thus, the invention contemplates a diagnostic tool in the form of a combination comprising two diagnostically active materials: at least one peptide and at least one dimer of said peptide. As further shown below, the at least one peptide comprises an amino acid having at least one sulfur atom, e.g., cysteine, and the dimer of said at least one peptide is formed by forming a covalent bond between a sulfur atom present on each of said at least one peptide. Thus, the dimer comprises a —S—S— bond.

By a first aspect, the present invention provides a composition comprising a compound of the general formula (I) in combination with a compound of the general Formula (Ia) and/or (Ib):

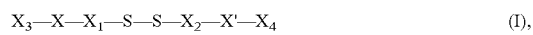

$$X_3—X—X_1—S—S—X_2—X'—X_4 \quad (I),$$

$$X_3—X—X_1—S—H \quad (Ia),$$

$$H—S—X_2—X'—X_4 \quad (Ib),$$

wherein:

—S—S— designates a disulfide group or a group comprising a disulfide;

each of X and X', independently of the other, may be absent or is each a pentapeptide comprising at least one amino acid selected from L, V and G;

each of $X_1$, $X_2$, $X_3$ and $X_4$, independently of the other, may be absent or is each an amino acid, a di-amino acid or a tri-amino acid;

each of said X, X', $X_1$, $X_2$, $X_3$ and $X_4$, independently of the other, is optionally substituted by at least one amino acid group;

each of "-" is a bond, wherein in the Formulae (Ia) and (Ib), each of X, $X_1$, $X_2$, $X_3$, $X_4$ and X' are selected as in Formula (I); and wherein the ratio between the compound of Formula (I) and the compound of Formula (Ia) or Formula (Ib) or a combination thereof is between about 1:1 to about 10:1. It has been observed that combinations of dimer and monomer in this range produce increasingly more robust, reproducible assay results.

As stated, the invention concerns a composition of at least two active peptide-based materials. The first being a compound of the general Formula (I), being a dimer containing a disulfide bond; and the other a peptide of the general Formula (Ia) and/or (Ib). The dimer utilized in a composition of the invention is typically selected to be a dimer of the peptide component of Formula (Ia) and/or (Ib). For example, where the peptide is of the general Formula (Ia): $X_3$—X—$X_1$—S—H, the dimer of Formula (I) is $X_3$—X—$X_1$—S—S—$X_1$—X—$X_3$. Similarly, where the peptide is of the general Formula (Ib): H—S—$X_2$—X'—$X_4$, the dimer of Formula (I) is $X_4$—X'—$X_2$—S—S—$X_2$—X'—$X_4$.

Putting it differently, where selecting a compound of Formula (I) and a compound of Formula (Ia) and/or (Ib), each of X, $X_1$, $X_2$, $X_3$, $X_4$ and X' are selected identically, such that the compound of Formula (I) is a dimer of at least one peptide of Formula (Ia) or Formula (Ib) present in the composition.

In some embodiments, where the combination is of a compound of Formula (I), a compound of Formula (Ia) and a compound of Formula (Ib), the dimer being a compound of Formula (I) is a dimer of the compound of Formula (Ia) or the compound of Formula (Ib).

The weight ratio between the at least two components of the composition, i.e., (1) a compound of the general Formula (I), and (2) a peptide of the general Formula (Ia) and/or (Ib) is at least 1:1. In some embodiments, the compound of the general Formula (I) is in excess. In some embodiments, the compound of the general Formula (I) exits in an amount which is at least twice as the amount of a peptide of the general Formula (Ia) and/or (Ib). In some embodiments, the amount of the compound of the general Formula (I) is 2, 3, 4, 5, 6, 7, 8, 9 or 10 times as much as a peptide of the general Formula (Ia) and/or (Ib).

In some embodiments, in a composition of the invention, the compound of the general Formula (I) constitutes at least 55% of the combination. In some embodiments, the compound of the general Formula (I) constitutes at least 50%, 55%, 60%, 65%, 70%, 75%, 80%, 85%, 90% or at least 95% of the active combination.

In other embodiments, in a composition of the invention, the compound of the general Formula (Ia) and/or (Ib) constitutes at most 50%, 45%, 40%, 35%, 30%, 25%, 20%, 15%, 10% or at most 5% of the active combination.

In some embodiments, the dimer of Formula (I) is asymmetric, namely it is a dimer of two different peptides, the peptide of the Formula (Ia) and/or (Ib) may be any of the two peptides making up the dimer.

Thus, when selecting a compound of Formula (I) for a composition of the invention, the identity of a peptide of Formula (Ia) or (Ib) may be easily determined.

As used herein an "amino acid" is any amino acid as known in the art. In some embodiments, the amino acid is any one of the 20 naturally occurring amino acids. In other embodiments, the amino acid is any of the 20 naturally occurring amino acids which is chemically modified. In further embodiments, the amino acid is a synthetic non-naturally occurring amino acid.

When referring to any one amino acid making up the peptides used in accordance with the invention, the amino acids may be referred to by their acceptable nomenclature or by their one-letter designation, as acceptable in the art. For example, the amino acid referred to by the letter L is Leucine. The amino acid referred to by the letter V is Valine. The amino acid referred to by the letter G is Glycine. The amino acid referred to by the letter K is Lysine. The amino acid referred to by the letter M is Methionine and the amino acid referred to by the letter C is Cysteine. Thus, in the exemplary peptide motif "LLVVG" is the peptide Leucine-Leucine-Valine-Valine-Glycine. Unless specifically indicated, the directionality of the peptide moiety or any peptide group depicted, may be either C→N or N→C.

In a compound of Formula (I), each of X and X', independently, may be a pentapeptide comprising five amino acids, each of the amino acids being connected to each other via a peptide bond. The pentapeptide is typically composed of the amino acids L, V and G, with one or more of same amino acids repeated along the sequence. In some embodiments, each of X and X', independently, may be a pentapeptide consisting of the amino acids L, V and G.

In some embodiments, each of X and X', when a pentapeptide, may be selected from the peptide sequences shown in Table 1.

In some embodiments, one of X and X' is absent and the other is a pentapeptide, as defined. In other embodiments, each of X and X' is a pentapeptide, which may or may not be the same. In some another embodiments, X and X' are different from each other.

In some embodiments, in a compound of Formula (I) and/or (Ia) and/or (Ib) one or both of X and X' are absent.

In some embodiments, the composition comprises a compound of Formula (I) which is selected amongst compounds having the structure:

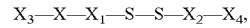

$X_3$—X—$X_1$—S—S—$X_2$—$X_4$,

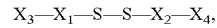

$X_3$—$X_1$—S—S—$X_2$—$X_4$,

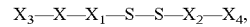

$X_3$—X—$X_1$—S—S—$X_2$—$X_4$, wherein in each of the above formulae, $X_3$, $X_1$, $X_2$ and $X_4$ are as defined.

In some embodiments, the compound of Formula (I) is a compound wherein X is absent and X' is as defined above, or a compound wherein both X and X' are absent or a compound wherein X is as defined above and X' is absent.

In the above formulae, each of $X_1$, $X_2$, $X_3$ and $X_4$, independently of the other, may be absent or is an amino acid, a di-amino acid or a tri-amino acid. As used herein, a di-amino acid is a dipeptide, namely two amino acids connected to each other via a peptide bond; a tri-amino acid is a tripeptide, namely three amino acids connected to each other via peptide bonds; wherein the amino acid in each of "amino acid", "di-amino acid" and "tri-amino acid" is as defined herein.

Each of the amino acids indicated in the general Formula (I) may be substituted by at least one amino acid group. The "at least one amino acid group" is a single amino acid or a chain of amino acids which are connected to each other, in some embodiments, via peptide bond(s); or a group comprising one or more amino acids. In some embodiments, the substituting amino acid group is or comprises an amino acid selected from C, K and M. In specific embodiments, the at least one amino acid group is C, K or M. In other embodiments, the at least one amino acid group comprises one or more of C, K and M.

In further embodiments, the amino acid group is C. In further embodiments, the amino acid group is K. In further embodiments, the amino acid group is M.

In some embodiments, the disulfide group is derived from cystine. In some embodiments, the cystine is substituted by at least one amino acid.

In some embodiments, each of $X_1$, $X_2$, $X_3$ and $X_4$, independently, is an amino acid, a di-amino acid or a tri-amino acid comprising an amino acid selected from K, C and M. In some embodiments, the amino acid is K.

In some embodiments, each of $X_1$ and $X_2$ are absent and $X_3$ and $X_4$, independently, is an amino acid, a di-amino acid or a tri-amino acid comprising an amino acid selected from K, C and M.

In some embodiments, each of $X_1$ and $X_2$, independently, is an amino acid, a di-amino acid or a tri-amino acid comprising an amino acid selected from K, C and M and $X_3$ and $X_4$ are absent. In some embodiments, at least one of $X_1$, $X_2$, $X_3$ and $X_4$, is absent.

In some embodiments, the composition of the invention comprises a compound having the general Formula (I), wherein each of $X_1$, $X_2$, $X_3$ and $X_4$, is absent; the compound being of the general Formula (II):

X—S—S—X'  (II)

wherein each of X and X' are as defined above.

In some embodiments, the disulfide group in the compound of Formula (II) is a cystine; the compound is of general Formula (III):

X—C(O)—CHY—CH$_2$—S—S—CH$_2$—CHY'—C(O)—X'  (III)

wherein each of X and X' are as defined above, —C(O)— designates a carbonyl group (—C=O), and each of Y and Y', independently of the other, is at least one amino acid, as defined herein. In some embodiments, each of Y and Y', independently, is selected from K, C and M.

In some embodiments, the composition comprises a compound of general Formula (I) having a general Formula (IV):

X—C(O)—CHY—CH$_2$—S—S—X'  (IV)

In other embodiments, the composition comprises a compound of Formula (I) having the structure of Formula (V):

X—S—S—CH$_2$—CHY'—C(O)—X'  (V)

wherein each of X and X' are as defined above, and Y' is at least one amino acid.

In some embodiments, each of X and X', independently of the other, is a pentapeptide comprising at least one amino acid L, at least one amino acid V and at least one amino acid G. In some embodiments, each of X and X', independently of the other, is a pentapeptide comprising at least two amino acids L. In some embodiments, wherein each of X and X', independently of the other, is a pentapeptide comprising at least two amino acids V. In some embodiments, each of X and X', independently of the other, is a pentapeptide selected from amino acid residues of Table 1.

TABLE 1

Possible 5-amino acid combinations (pentapeptides) employed in accordance with derivatives of the invention. The peptide connectivity may be read from right to left or from left to right.

| | | | | | |
|---|---|---|---|---|---|
| L | L | V | V | G | SEQ ID NO: 1 |
| L | L | V | G | V | SEQ ID NO: 2 |
| L | L | G | V | V | SEQ ID NO: 3 |
| L | V | L | V | G | SEQ ID NO: 4 |
| L | V | L | G | V | SEQ ID NO: 5 |
| L | G | L | V | V | SEQ ID NO: 6 |
| L | V | V | L | G | SEQ ID NO: 7 |
| L | V | G | L | V | SEQ ID NO: 8 |
| L | G | V | L | V | SEQ ID NO: 9 |
| L | V | V | G | L | SEQ ID NO: 10 |
| L | V | G | V | L | SEQ ID NO: 11 |
| L | G | V | V | L | SEQ ID NO: 12 |
| V | L | L | V | G | SEQ ID NO: 13 |
| V | L | L | G | V | SEQ ID NO: 14 |
| G | L | L | V | V | SEQ ID NO: 15 |
| V | L | V | L | G | SEQ ID NO: 16 |
| V | L | G | L | V | SEQ ID NO: 17 |
| G | L | V | L | V | SEQ ID NO: 18 |
| V | L | V | G | L | SEQ ID NO: 19 |
| V | L | G | V | L | SEQ ID NO: 20 |
| G | L | V | V | L | SEQ ID NO: 21 |
| V | V | L | L | G | SEQ ID NO: 22 |
| V | G | L | L | V | SEQ ID NO: 23 |
| G | V | L | L | V | SEQ ID NO: 24 |
| V | V | L | G | L | SEQ ID NO: 25 |
| V | G | L | V | L | SEQ ID NO: 26 |
| G | V | L | V | L | SEQ ID NO: 27 |
| V | V | G | L | L | SEQ ID NO: 28 |
| V | G | V | L | L | SEQ ID NO: 29 |
| G | V | V | L | L | SEQ ID NO: 30 |

In some embodiments, each X and X' independently of the other, is selected from the amino acid residues: LLVVG (SEQ ID NO: 1), LLVGV (SEQ ID NO: 2), LLGVV (SEQ ID NO: 3), LVLVG (SEQ ID NO: 4), LVLGV (SEQ ID NO: 5), LGLVV (SEQ ID NO: 6), LVVLG (SEQ ID NO: 7), LVGLV (SEQ ID NO: 8), LGVLV (SEQ ID NO: 9), LVVGL (SEQ ID NO: 10), LVGVL (SEQ ID NO: 11), LGVVL (SEQ ID NO: 12), VLLVG (SEQ ID NO: 13), VLLGV (SEQ ID NO: 14), GLLVV (SEQ ID NO: 15), VLVLG (SEQ ID NO: 16), VLGLV (SEQ ID NO: 17), GLVLV (SEQ ID NO: 18), VLVGL (SEQ ID NO: 19), VLGVL (SEQ ID NO: 20), GLVVL (SEQ ID NO: 21), VVLLG (SEQ ID NO: 22), VGLLV (SEQ ID NO: 23), GVLLV (SEQ ID NO: 24), VVLGL (SEQ ID NO: 25), VGLVL (SEQ ID NO: 26), GVLVL (SEQ ID NO: 27), VVGLL (SEQ ID NO: 28), VGVLL (SEQ ID NO: 29) and GVVLL (SEQ ID NO: 30).

In some embodiments, each X and X' independently of the other, is selected from LLVVG (SEQ ID NO: 1), LGVVL (SEQ ID NO: 12), VLLVG (SEQ ID NO: 13), VLLGV (SEQ ID NO: 14), VVLLG (SEQ ID NO: 22), VGLLV (SEQ ID NO: 23) and GVLLV (SEQ ID NO: 24).

In some embodiments, each X and X' independently of the other, is selected from VLVGL (SEQ ID NO: 19), VLGVL (SEQ ID NO: 20), LVVLG (SEQ ID NO: 7), LVGLV (SEQ ID NO: 8), LGVLV (SEQ ID NO: 9), LVVGL (SEQ ID NO: 10), GVLLV (SEQ ID NO: 24) and LGVVL (SEQ ID NO: 12).

In some embodiments, each X and X' independently of the other, is selected from VLLGV (SEQ ID NO: 14), GLLVV (SEQ ID NO: 15), VVLGL (SEQ ID NO: 25), VGLVL (SEQ ID NO: 26), LLVVG (SEQ ID NO: 1), LLVGV (SEQ ID NO: 2) and LGVVL (SEQ ID NO: 12).

In some embodiments, each X and X' independently of the other, is selected from LGVVL (SEQ ID NO: 12) and LVVGL (SEQ ID NO: 10).

In some embodiments, one or both of X and X' in any one of the Formulae (I)-(V) is -LGVVL (SEQ ID NO: 12).

In some embodiments, the composition of the invention comprises a compound of Formula (I) having the general Formula (VI) or (VII):

X—C(O)—CHY—CH$_2$—S—S—CH$_2$—CHY'—C(O)-LGVVL(SEQ ID NO:12)  (VI)

LVVGL-C(O)—CHY—CH$_2$—S—S—CH$_2$—CHY'—C(O)—X'(SEQ ID NO: 10)  (VII)

wherein each of X, X', Y and Y', independently of the other, is as defined above.

In some embodiments, one or both Y and Y' in the Formulae (III)-(VII) is the amino acid K. In some embodiments, Y=Y' in the Formulae (III)-(VII) and is the amino acid K.

In some embodiments, X and X' in any one of the formulae of the invention, independently, is a pentapeptide selected from LLVVG (SEQ ID NO: 1), LLVGV (SEQ ID NO: 2), LLGVV (SEQ ID NO: 3), LVLVG (SEQ ID NO: 4), LVLGV (SEQ ID NO: 5), LGLVV (SEQ ID NO: 6), LVVLG (SEQ ID NO: 7), LVGLV (SEQ ID NO: 8), LGVLV (SEQ ID NO: 9), LVVGL (SEQ ID NO: 10), LVGVL (SEQ ID NO: 11), LGVVL (SEQ ID NO: 12), VLLVG (SEQ ID NO: 13), VLLGV (SEQ ID NO: 14), GLLVV (SEQ ID NO: 15), VLVLG (SEQ ID NO: 16), VLGLV (SEQ ID NO: 17), GLVLV (SEQ ID NO: 18), VLVGL (SEQ ID NO: 19), VLGVL (SEQ ID NO: 20), GLVVL (SEQ ID NO: 21), VVLLG (SEQ ID NO: 22), VGLLV (SEQ ID NO: 23), GVLLV (SEQ ID NO: 24), VVLGL (SEQ ID NO: 25), VGLVL (SEQ ID NO: 26), GVLVL (SEQ ID NO: 27), VVGLL (SEQ ID NO: 28), VGVLL (SEQ ID NO: 29) and GVVLL (SEQ ID NO: 30).

In some embodiments, X and X' of any one of the formulae of the invention, independently, is a pentapeptide selected from VVGLL (SEQ ID NO: 28), VGLLV (SEQ ID NO: 23), GLLVV (SEQ ID NO: 15), LVGVL (SEQ ID NO: 11), LVVGL (SEQ ID NO: 10), LGVVL (SEQ ID NO: 12), GVLVL (SEQ ID NO: 27) and GLLV (SEQ ID NO: 23).

In some embodiments, the composition of the invention comprises a compound (VI), as defined herein, in combination with LVVGL-C(O)—CHY—CH$_2$—S—H (SEQ ID NO: 10) or H—S—CH$_2$—CHY'—C(O)—X'.

In other embodiments, the composition of the invention comprises a compound (VII), as defined herein, in combination with X—C(O)—CHY—CH$_2$—S—H or H—S—CH$_2$—CHY'—C(O)-LGVVL (SEQ ID NO: 12).

In some embodiments, the composition of the invention comprises the compound of Formula (VIII):

LVVGL-CO—CH(NH—K)—CH$_2$—S—S—CH$_2$—CH(NH—K)—CO-LGVVL(SEQ ID NO: 10;SEQ ID NO: 12)  (VIII).

An embodiment of this dimer is:

(I)

An embodiment of the peptide (Formula (Ia)) is LVVGL-CK (SEQ. ID NO: 31).

In the compound of Formula (VIII), the group (NH—K) is pendant and covalently bonded to the carbon atom of the —CH— moiety. The amino acid K is bonded only to the —NH— group which is linking the amino acid K and —CH—.

In some embodiments, the composition comprises the compound of Formula (VIII) in combination with the peptide LVVGL-CO—CH(NH—K)—CH$_2$—SH (SEQ ID NO: 10).

In some embodiments, the compound of any of Formulae (I) to (VIII) is provided associated to biotin.

In some embodiments, the compounds of Formulae (Ia) and (Ib) are provided associated to biotin.

In some embodiments, the compound of Formula (I) is the compound of Formula (VIII) when associated with biotin:
Biotin-LVVGL-CO—CH(NH—K)—CH$_2$—S—S—CH$_2$—CH(NH—K)—CO-LGVVL-Biotin (SEQ ID NO: 10; SEQ ID NO: 12).

In another aspect, the invention provides use of at least one compound of Formula (I) and at least one compound of Formula (Ia) and/or (Ib), for the preparation of a diagnostic composition.

In a further aspect, there is provided a combination of at least one compound of Formula (I) and at least one compound of Formula (Ia) and/or (Ib) for use in a method of diagnosis.

In some embodiments, the composition is for the diagnosis of schizophrenia in an individual being, in some embodiments, a child under the age of 18.

In another aspect, the invention provides a method for the diagnosis of schizophrenia in a subject, the method comprising:
contacting a blood sample obtained from a subject suspected of developing Schizophrenia with a composition according to the invention, as defined herein;
determining the level of binding of the peptide components present in the composition to said sample, such that a level higher than the binding level of said peptide components to a sample from non-schizophrenic individuals indicating that said subject has a high likelihood of having schizophrenia. As any composition of the invention may comprise two or more peptide-based materials, as defined herein, the binding may be of any one or more of said peptide-based materials.

As readily realized by the person of skill in the art, the herein defined diagnosis, i.e. the determination of the level of binding of the peptide components present in the composition to said sample, may be achieved by a number of (e.g. chemical, biological) detection methods common to the pertinent field of the art that employ binding of peptides to generate a measurable signal which, based thereupon, diagnosis of schizophrenia is achieved. Some non-limiting examples of detection methods which can be used include enzyme-linked immunosorbent assay (ELISA), bimolecular fluorescence complementation (BiFC), chemical cross-linking followed by high mass matrix-assisted laser desorption/ionization mass spectrometry, proximity ligation assay (PLA), dual polarization interferometry (DPI), static light scattering (SLS), surface plasmon resonance, fluorescence polarization/anisotropy, fluorescence correlation spectroscopy, fluorescence resonance energy transfer (FRET), protein-protein docking, isothermal titration calorimetry (ITC) and microscale thermophoresis (MST).

In some embodiments, the method is for use in confirming a high probability of Schizophrenia in an individual determined by at least one other diagnostic assay.

In some embodiments, the detection method is ELISA.

In another aspect, the invention provides a kit for use in the diagnosis of Schizophrenia, the kit comprising a support comprising one or more peptide-based materials defined herein, immobilized onto an anti-human immunoglobulin (hIg) antibody or fragment thereof, reagents for carrying out a detection assay comprising e.g. an anti-human immunoglobin (hIg) antibody or fragment thereof bound to a chemiluminescent tag or an enzyme such as alkaline phosphatase or horseradish peroxidase, and instructions for use.

As readily recognized by the skilled artesian, the kit and diagnostic composition of the present invention may also contain additional reagents and components suitable for using said kit and diagnostic composition in the herein described diagnosis of Schizophrenia. Some non-limiting examples of such reagents and components include a buffer, a diluent, a carrier, a chemical stabilizer, a preservative, a salt, an enzyme, a detection reagent, a pretreatment reagent/solution, a substrate (e.g., as a solution) and a stop solution.

The kit of the present invention may also contain reagent reservoirs and any additional component (e.g. disposable pipettes) required for using said kit in the herein described diagnosis of Schizophrenia.

In some embodiments, the anti-hIg antibody is complexed to a detectable marker. In some embodiments, instead of said anti-hIg antibody, the kit comprises one or more non-bound peptide-based materials which bind to PAA present in a tested sample, said peptide-based materials being complexed to a detectable marker.

EXAMPLES

Example 1: Dimerization of the Peptide Vs. Sensitivity of the Assay

Portions of 10 µl of each of peptide samples I-X, were used for MALDI-MS analysis, to estimate the ratio of mono-versus dimer formed.

As can be seen from Table 2, using the 20% DMSO/80% DDW solvent system, after 8 hours, about 80-90% of the peptide was in the dimer form.

It should be noted that slightly basic conditions expedited the dimerization/oxidation of cysteine residues. For this purpose, ammonia solution was added before the reaction occurred. Diluted ammonia was useful in pushing the formation of the dimer to completeness. All samples were analyzes by MALDI-MS technique.

TABLE 2

Dimerization of the peptide vs. sensitivity of the assay (ACN = Acetonitrile; DDW = Double Distilled Water; TFA = Trifluoroacetic Acid; TFE = Trifluoroethanol; DMSO = Dimethyl Sulfoxide).
The data in Table 2 were obtained by using low capacity Streptavidin (SA) coated tubes.

| Solvent | Peptide Concentration mg/ml (stock solution) | Dimerization time | Percent of dimer formed (%) | Sensitivity of the assay (%) |
|---|---|---|---|---|
| ACN/DDW | 0.35 | 4 hr RT | 20-25 | 14-22 |
| ACN/DDW | 0.35 | 8 hr RT | 15-20 | 19-24 |
| ACN/DDW | 0.35 | 18 hr RT | 15-20 | 19-24 |
| ACN/TFA/TFE | 0.4 | 8 hr RT | 0-5 | 17-19 |
| ACN/NaHCO$_3$ | 0.12 | 4 hr RT | 40-45 | 45-51 |
| ACN/NaHCO$_3$ | 0.12 | 18 hr RT | 55-60 | 44-55 |
| 20% DMSO 80% DDW | 0.4 | 4 hr RT | 75 | 55-61 |
| 20% DMSO 80% DDW | 0.4 | 8 hr RT | 80-90 | 58-61 |
| 20% DMSO 80% DDW | 0.4 | 18 hr RT | 80-90 | 58-61 |
| 20% DMSO 80% DDW | 0.4 | 24 hr RT | 80-90 | 58-61 |
| 28% DMSO 72% DDW | 1.5 | 8-18 hr RT | 80-90 | 61-84 |

The data in Table 2 were obtained by using high capacity Streptavidin (SA) coated tubes of. Under these improved experimental conditions, the OD values were raised from 1.6-1.7 to more than 2.5. The spacer arm between biotin-peptide was modified. Instead of "standard LC" (amino-hexanoic acid), the stretch -SGSG- (Serine-Glycine-Serine-Glycine) has been used.

Example 2: Use of a Mixture Comprising 80-90% of the Herein Described Dimer in a Screening Blood Test for the Diagnosis of Schizophrenia Via Measurement of PAA Levels in Young Schizophrenic Patients at Onset of Disease Blood titers of PAA were evaluated blindly using an optimized ELISA test, wherein the results were expressed using a linear optical density (OD) scale. OD readings were scored for blood samples from pediatric/young adult patients (n=28) (aged 13-19 years) diagnosed with schizophrenia and controls (n=37) (aged 13-19 years). The blood samples of all participants were tested anonymously and were scored under a code number. A test recording above 1.4 OD units was defined as positive.

Tables 3-5 show results of screening tests for both pediatric/young adult (age 13-19 years) patients and controls.

TABLE 3

Screening results for pediatric/young adult patients (13-19 years)
Young Patients (13-19 years)

| Number of Patient | Age | Gender (F/M) | OD | Conclusion | Remarks |
|---|---|---|---|---|---|
| 1 | 18 | M | 1.84 | Positive | |
| 2 | 17 | F | 1.86 | Positive | Before treatment by Leponex |
| 3 | 16 | M | 0.87 | Negative | Before treatment by Leponex |
| 4 | 13 | F | 2.42 | High Positive | Before treatment by Leponex |
| 5 | 19 | M | 2.48 | High Positive | Before treatment by Leponex |
| 6 | 19 | F | 1.88 | Positive | Before treatment by Leponex |
| 7 | 17 | M | 0.95 | Negative | |
| 8 | 18 | M | 2.24 | High Positive | Before treatment by Leponex |
| 9 | 14 | F | 1.36 | Negative | |
| 10 | 16 | M | 1.36 | Negative | |
| 11 | 18 | M | 0.88 | Negative | |
| 12 | 13 | M | 1.23 | Negative | |
| 13 | 18 | M | 2.36 | High Positive | |
| 14 | 16 | M | 1.08 | Negative | |
| 15 | 14 | M | 0.98 | Negative | |
| 16 | 16 | M | 2.36 | High Positive | Before treatment by Leponex |
| 17 | 18 | F | 2.28 | High Positive | Before treatment by Leponex |
| 18 | 16 | M | 1.18 | Negative | |
| 19 | 18 | F | 1.75 | Positive | |
| 20 | 19 | M | 1.81 | Positive | |
| 21 | 17 | M | 1.06 | Negative | |
| 22 | 16 | M | 2.02 | High Positive | |
| 23 | 14 | M | 2.21 | High Positive | |
| 24 | 13 | M | 2.32 | High Positive | |
| 25 | 19 | M | 1.72 | Positive | |
| 26 | 17 | M | 1.93 | High Positive | |
| 27 | 15 | M | 1.24 | Negative | |
| 28 | 17 | F | 2.35 | High Positive | |
| | | Mean | 1.72 | | |
| | | SD | 0.55 | | |

TABLE 4

Screening results for pediatric/young adult controls (13-19 years)
Pediatric/Young Adult Controls (13-19 years)

| Number of Control | Age | Gender (F/M) | OD | Conclusion |
|---|---|---|---|---|
| 1 | 15 | M | 0.64 | |
| 2 | 17 | F | 0.73 | |
| 3 | 17 | M | 1.86 | Positive |
| 4 | 16 | M | 0.53 | |
| 5 | 16 | M | 0.97 | |
| 6 | 13 | M | 2.04 | High Positive |
| 7 | 13 | M | 0.41 | |
| 8 | 16 | M | 1.12 | |
| 9 | 18 | M | 0.86 | |
| 10 | 14 | F | 1.27 | |
| 11 | 13 | M | 0.64 | |
| 12 | 16 | M | 0.7 | |
| 13 | 13 | M | 0.95 | |
| 14 | 13 | M | 0.93 | |
| 15 | 16 | F | 1.69 | Positive |
| 16 | 15 | F | 0.78 | |
| 17 | 16 | F | 0.53 | |
| 18 | 17 | F | 1.91 | High Positive |
| 19 | 14 | F | 0.99 | |
| 20 | 16 | F | 0.62 | |
| 21 | 16 | F | 0.97 | |
| 22 | 13 | M | 1.24 | |
| 23 | 14 | M | 0.78 | |

TABLE 4-continued

Screening results for pediatric/young adult controls (13-19 years)
Pediatric/Young Adult Controls (13-19 years)

| Number of Control | Age | Gender (F/M) | OD | Conclusion |
|---|---|---|---|---|
| 24 | 13 | M | 1.39 | |
| 25 | 15 | F | 1.72 | Positive |
| 26 | 13 | F | 1.18 | |
| 27 | 13 | M | 1.04 | |
| 28 | 17 | F | 1.36 | |
| 29 | 16 | M | 0.95 | |
| 30 | 17 | M | 0.6 | |
| 31 | 14 | F | 1.21 | |
| 32 | 19 | M | 1.81 | Positive |
| 33 | 18 | M | 0.87 | |
| 34 | 17 | M | 1.09 | |
| 35 | 17 | F | 0.92 | |
| 36 | 18 | M | 1.33 | |
| 37 | 17 | F | 0.59 | |
| | Mean | | 1.06 | |
| | SD | | 0.43 | |

TABLE 5A-B provide summaries of the pediatric/young adult patient and control screening study.

A. Summary of the results

| Pediatric/Young Adult Patients N=28 | | Pediatric/Young Adult Controls N=37 | | P value |
|---|---|---|---|---|
| Positive | 17 | Positive | 6 | P < 1.05 × 10$^{-6}$ |
| Negative | 11 | Negative | 31 | |
| Sensitivity % | 60.7 | Specificity % | 83.8 | |

B. OD Range

| | |
|---|---|
| Negative | ≤1.4 |
| Low Positive (Grey-Zone) | 1.4-1.6 |
| Positive | 1.6-1.9 |
| High Positive | ≥1.9 |

As may be evident from the above Tables, PAA titers of young schizophrenia patients, aged 13-19 years, were significantly higher than those of the control group (1.72±0.55 OD units vs. 1.06±0.43; $P<1.05\times10^{-6}$).

Example 3: Data on Non-Schizophrenic Pediatric/Young Adult Patients

TABLE 6

Non-schizophrenic pediatric and young adult patients.

| Number of Patient | Gender (F/M) | Age | OD | Conclusion | Diagnosis (as assessed by clinical team) |
|---|---|---|---|---|---|
| 1 | M | 15 | 0.682 | Negative | Mental retardation |
| 2 | M | 17 | 1.03 | Negative | Mental retardation |
| 3 | M | 16 | 1.08 | Negative | Mental retardation |
| 4 | F | 16 | 1.03 | Negative | Mental retardation |
| 5 | F | 16 | 0.548 | Negative | Mental retardation |
| 6 | F | 15 | 0.807 | Negative | Mental retardation |
| 7 | F | 14 | 0.681 | Negative | Pervasive Developmental Disorder (PDD) |
| 8 | M | 18 | 0.89 | Negative | PDD |
| 9 | F | 15 | 1.176 | Negative | Bipolar |
| 10 | M | 17 | 0.597 | Negative | Bipolar |
| 11 | M | 19 | 0.53 | Negative | Bipolar |
| 12 | F | 17 | 0.982 | Negative | Bipolar |
| 13 | F | 16 | 0.527 | Negative | Bipolar |
| 14 | F | 16 | 0.442 | Negative | Bipolar |
| 15 | F | 18 | 1.09 | Negative | Depression |
| 16 | M | 14 | 0.742 | Negative | Depression |
| 17 | F | 19 | 0.662 | Negative | Depression |
| 18 | M | 18 | 0.712 | Negative | Depression |
| 19 | M | 15 | 0.964 | Negative | Obsessive-Compulsive Disorder (OCD) |
| 20 | F | 16 | 1.015 | Negative | OCD |
| 21 | M | 15 | 0.443 | Negative | OCD |
| 22 | M | 15 | 0.583 | Negative | OCD |
| 23 | F | 18 | 0.864 | Negative | OCD |
| 24 | M | 19 | 1.12 | Negative | OCD |
| 25 | M | 17 | 1.78 | Positive | Borderline |
| 26 | F | 16 | 0.889 | Negative | Borderline |
| 27 | F | 17.5 | 0.541 | Negative | Borderline |
| 28 | F | 14 | 0.892 | Negative | Borderline |
| 29 | F | 16 | 1.09 | Negative | Borderline |
| 30 | F | 15 | 0.301 | Negative | Borderline |
| 31 | F | 17 | 1.206 | Negative | Borderline |
| 32 | F | 15 | 0.891 | Negative | Borderline |
| 33 | F | 15 | 0.432 | Negative | Borderline |
| 34 | M | 17 | 0.41 | Negative | Borderline |
| 35 | F | 19 | 0.621 | Negative | Borderline |
| 36 | F | 17 | 0.584 | Negative | Borderline |
| 37 | M | 14 | 0.507 | Negative | Conduct disorder[a] |
| 38 | F | 16 | 0.386 | Negative | Personal disorder[b] |

TABLE 6-continued

Non-schizophrenic pediatric and young adult patients.

| Number of Patient | Gender (F/M) | Age | OD | Conclusion | Diagnosis (as assessed by clinical team) |
|---|---|---|---|---|---|
| 39 | F | 17 | 1.18 | Negative | Personal disorder |
| 40 | F | 14 | 0.873 | Negative | Conduct disorder |
| 41 | M | 13 | 1.89 | Positive | Conduct disorder |
| 42 | M | 13 | 1.14 | Negative | Conduct disorder |
| 43 | F | 15.5 | 0.286 | Negative | Conduct disorder |
| 44 | M | 14 | 0.432 | Negative | Conduct disorder |
| 45 | F | 16 | 0.943 | Negative | Conduct disorder |
| 46 | M | 14 | 0.296 | Negative | Conduct disorder |
| 47 | M | 16 | 0.712 | Negative | Personal disorder |
| 48 | M | 16 | 0.445 | Negative | Conduct disorder |
| 49 | M | 12 | 0.478 | Negative | Conduct disorder |
| 50 | F | 14 | 1.112 | Negative | Conduct disorder |
| 51 | F | 14 | 0.501 | Negative | Conduct disorder |
| 52 | F | 16 | 0.964 | Negative | Conduct disorder |
| 53 | F | 16 | 0.621 | Negative | Conduct disorder |
| 54 | M | 14 | 0.851 | Negative | Conduct disorder |
| 55 | F | 15 | 0.329 | Negative | Conduct disorder |
| 56 | F | 18 | 0.815 | Negative | Personal disorder |
| 57 | M | 15 | 1.922 | Positive | Conduct disorder |
| 58 | F | 18 | 0.644 | Negative | Personal disorder |
| 59 | M | 18 | 0.543 | Negative | Personal disorder |
| 60 | F | 18 | 0.602 | Negative | Personal disorder |
| 61 | M | 15 | 0.453 | Negative | Conduct disorder |
| 62 | M | 14 | 0.369 | Negative | Conduct disorder |
|  |  | Mean | 0.77 |  |  |
|  |  | SD | 0.36 |  |  |

[a]Conduct disorder (CD) is a psychological disorder diagnosed in childhood or adolescence (ages 0-17) that presents itself through a repetitive and persistent pattern of behavior in which the basic rights of others or major age-appropriate norms are violated. These behaviors are often referred to as "antisocial behaviors." It is often seen as the precursor to antisocial personality disorder, which is not diagnosed until the individual is 18 years old.
[b]Personal (Personality) disorders are a class of mental disorders characterized by enduring maladaptive patterns of behavior, cognition, and inner experience, exhibited across many contexts and deviating markedly from those accepted by the individual's culture (ages 18 upwards).

As may be evident from Table 6, only 3/62 cases of non-schizophrenic pediatric and young adult patients between the ages of 12-19 tested positive using this schizophrenic diagnostic test showing that the herein described method for diagnosing schizophrenia constitutes a reliable assay (with a low, approximately 5%, of false positives) for differentiating between schizophrenia and other non-schizophrenic disorders (such as personal and conduct disorder).

The invention claimed is:

1. A method for the diagnosis of schizophrenia in a subject, the method comprising:
   a) contacting a subject blood sample obtained from a subject suspected of developing schizophrenia with a composition;
   b) determining the level of binding of said dimer of the peptide of Formula (I) and peptide (Ia) to said patient sample by ELISA;
   c) determining the level of binding of said dimer of the peptide of Formula (I) and peptide (Ia) to a control sample by ELISA,
      wherein when the level of binding in said subject blood sample is higher than the level in said control sample indicates that said individual has a high likelihood of having schizophrenia,
      wherein when the level of binding in said subject blood sample is lower than the level of binding in said control sample indicates that said individual has a low likelihood of having schizophrenia, and
   wherein the composition comprises a dimer of a peptide, the dimer having the general formula (I):

$$\begin{array}{c} \text{LVVGL—CK} \\ | \\ \text{LVVGL—CK} \end{array} \quad (I)$$

and the peptide having the Formula (Ia):

LVVGL-CK     (Ia)(SEQ. ID NO:31)

wherein:
the C (cysteine) residues are bonded via a disulfide bond; and wherein
at least 50 wt % of the peptide is present in the composition as the dimer of the peptide, wherein sensitivity of the ELISA is improved over another ELISA performed with a second composition comprising 25% or less of the dimer of the peptide.

2. The method according to claim 1, wherein at least 75 wt % of the peptide is present in the composition as the dimer of the peptide.

3. The method according to claim 1, wherein at least 80 wt % of the peptide is present in the composition as the dimer of the peptide.

4. The method according to claim 1, wherein the amount of the compound of Formula (I) relative to the amount of the compound of Formula (Ia) is between 80 and 90 wt %.

5. The method according to claim 1, wherein at least 55% of the peptide is present in the composition as the dimer of the peptide.

6. A method for the diagnosis of schizophrenia in a subject, the method comprising:
a) contacting a subject blood sample obtained from a subject suspected of developing schizophrenia with a composition;
b) determining the level of binding of said dimer of the peptide of Formula (I) and peptide (Ia) to said patient sample by ELISA wherein at least 75 wt % of the peptide (Ia) is present in the composition as the dimer of the peptide of Formula (I);
c) determining the level of binding of said dimer of the peptide of Formula (I) and peptide (Ia) to a control sample by ELISA wherein at least 75 wt % of the peptide (Ia) is present in the composition as the dimer of the peptide of Formula (I),
wherein when the level of binding in said subject blood sample is higher than the level in said control sample indicates that said individual has a high likelihood of having schizophrenia, and
wherein when the level of binding in said subject blood sample is lower than the level of binding in said control sample indicates that said individual has a low likelihood of having schizophrenia, and
further comprising
confirming a high probability of Schizophrenia in an individual determined by at least one other diagnostic assay to have a high probability of Schizophrenia, and
wherein the composition comprises a dimer of a peptide, the dimer having the general formula (I):

and the peptide having the Formula (Ia):

wherein:
the C (cysteine) residues are bonded via a disulfide bond; and wherein
at least 50 wt % of the peptide is present in the composition as the dimer of the peptide, wherein sensitivity of the ELISA is improved over another ELISA performed with a second composition comprising 25% or less of the dimer of the peptide.

7. The method according to claim 6, wherein at least 75% of the peptide is present in the composition as the dimer of the peptide.

8. The method according to claim 6, wherein at least 55% of the peptide is present in the composition as the dimer of the peptide.

9. The method according to claim 6, wherein at least 80% of the peptide is present in the composition as the dimer of the peptide.

10. The method according to claim 6, wherein the amount of the compound of Formula (I) relative to the amount of the compound of Formula (Ia) is between 80 and 90 wt %.

* * * * *

SEQUENCE LISTING

```
<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: pentapeptide component

<400> SEQUENCE: 1

Leu Leu Val Val Gly
1               5

<210> SEQ ID NO 2
<211> LENGTH: 5
<212> TYPE: PRT
<213> ORGANISM: Artificial Sequence
<220> FEATURE:
<223> OTHER INFORMATION: pentapeptide component

<400> SEQUENCE: 2

Leu Leu Val Gly Val
1               5

<210> SEQ ID NO 3
```

```
<211> LENGTH: 5
<212> TYPE: PRT
<213> ORGANISM: Artificial Sequence
<220> FEATURE:
<223> OTHER INFORMATION: pentapeptide component

<400> SEQUENCE: 3

Leu Leu Gly Val Val
1               5

<210> SEQ ID NO 4
<211> LENGTH: 5
<212> TYPE: PRT
<213> ORGANISM: Artificial Sequence
<220> FEATURE:
<223> OTHER INFORMATION: pentapeptide component

<400> SEQUENCE: 4

Leu Val Leu Val Gly
1               5

<210> SEQ ID NO 5
<211> LENGTH: 5
<212> TYPE: PRT
<213> ORGANISM: Artificial Sequence
<220> FEATURE:
<223> OTHER INFORMATION: pentapeptide component

<400> SEQUENCE: 5

Leu Val Leu Gly Val
1               5

<210> SEQ ID NO 6
<211> LENGTH: 5
<212> TYPE: PRT
<213> ORGANISM: Artificial Sequence
<220> FEATURE:
<223> OTHER INFORMATION: pentapeptide component

<400> SEQUENCE: 6

Leu Gly Leu Val Val
1               5

<210> SEQ ID NO 7
<211> LENGTH: 5
<212> TYPE: PRT
<213> ORGANISM: Artificial Sequence
<220> FEATURE:
<223> OTHER INFORMATION: pentapeptide component

<400> SEQUENCE: 7

Leu Val Val Leu Gly
1               5

<210> SEQ ID NO 8
<211> LENGTH: 5
<212> TYPE: PRT
<213> ORGANISM: Artificial Sequence
<220> FEATURE:
<223> OTHER INFORMATION: pentapeptide component

<400> SEQUENCE: 8

Leu Val Gly Leu Val
1               5

<210> SEQ ID NO 9
<211> LENGTH: 5
```

```
<212> TYPE: PRT
<213> ORGANISM: Artificial Sequence
<220> FEATURE:
<223> OTHER INFORMATION: pentapeptide component

<400> SEQUENCE: 9

Leu Gly Val Leu Val
1               5

<210> SEQ ID NO 10
<211> LENGTH: 5
<212> TYPE: PRT
<213> ORGANISM: Artificial Sequence
<220> FEATURE:
<223> OTHER INFORMATION: pentapeptide component

<400> SEQUENCE: 10

Leu Val Val Gly Leu
1               5

<210> SEQ ID NO 11
<211> LENGTH: 5
<212> TYPE: PRT
<213> ORGANISM: Artificial Sequence
<220> FEATURE:
<223> OTHER INFORMATION: pentapeptide component

<400> SEQUENCE: 11

Leu Val Gly Val Leu
1               5

<210> SEQ ID NO 12
<211> LENGTH: 5
<212> TYPE: PRT
<213> ORGANISM: Artificial Sequence
<220> FEATURE:
<223> OTHER INFORMATION: pentapeptide component

<400> SEQUENCE: 12

Leu Gly Val Val Leu
1               5

<210> SEQ ID NO 13
<211> LENGTH: 5
<212> TYPE: PRT
<213> ORGANISM: Artificial Sequence
<220> FEATURE:
<223> OTHER INFORMATION: pentapeptide component

<400> SEQUENCE: 13

Val Leu Leu Val Gly
1               5

<210> SEQ ID NO 14
<211> LENGTH: 5
<212> TYPE: PRT
<213> ORGANISM: Artificial Sequence
<220> FEATURE:
<223> OTHER INFORMATION: pentapeptide component

<400> SEQUENCE: 14

Val Leu Leu Gly Val
1               5

<210> SEQ ID NO 15
<211> LENGTH: 5
<212> TYPE: PRT
```

```
<213> ORGANISM: Artificial Sequence
<220> FEATURE:
<223> OTHER INFORMATION: pentapeptide component

<400> SEQUENCE: 15

Gly Leu Leu Val Val
1               5

<210> SEQ ID NO 16
<211> LENGTH: 5
<212> TYPE: PRT
<213> ORGANISM: Artificial Sequence
<220> FEATURE:
<223> OTHER INFORMATION: pentapeptide component

<400> SEQUENCE: 16

Val Leu Val Leu Gly
1               5

<210> SEQ ID NO 17
<211> LENGTH: 5
<212> TYPE: PRT
<213> ORGANISM: Artificial Sequence
<220> FEATURE:
<223> OTHER INFORMATION: pentapeptide component

<400> SEQUENCE: 17

Val Leu Gly Leu Val
1               5

<210> SEQ ID NO 18
<211> LENGTH: 5
<212> TYPE: PRT
<213> ORGANISM: Artificial Sequence
<220> FEATURE:
<223> OTHER INFORMATION: pentapeptide component

<400> SEQUENCE: 18

Gly Leu Val Leu Val
1               5

<210> SEQ ID NO 19
<211> LENGTH: 5
<212> TYPE: PRT
<213> ORGANISM: Artificial Sequence
<220> FEATURE:
<223> OTHER INFORMATION: pentapeptide component

<400> SEQUENCE: 19

Val Leu Val Gly Leu
1               5

<210> SEQ ID NO 20
<211> LENGTH: 5
<212> TYPE: PRT
<213> ORGANISM: Artificial Sequence
<220> FEATURE:
<223> OTHER INFORMATION: pentapeptide component

<400> SEQUENCE: 20

Val Leu Gly Val Leu
1               5

<210> SEQ ID NO 21
<211> LENGTH: 5
<212> TYPE: PRT
<213> ORGANISM: Artificial Sequence
```

-continued

```
<220> FEATURE:
<223> OTHER INFORMATION: pentapeptide component

<400> SEQUENCE: 21

Gly Leu Val Val Leu
1               5

<210> SEQ ID NO 22
<211> LENGTH: 5
<212> TYPE: PRT
<213> ORGANISM: Artificial Sequence
<220> FEATURE:
<223> OTHER INFORMATION: pentapeptide sequence

<400> SEQUENCE: 22

Val Val Leu Leu Gly
1               5

<210> SEQ ID NO 23
<211> LENGTH: 5
<212> TYPE: PRT
<213> ORGANISM: Artificial Sequence
<220> FEATURE:
<223> OTHER INFORMATION: pentapeptide component

<400> SEQUENCE: 23

Val Gly Leu Leu Val
1               5

<210> SEQ ID NO 24
<211> LENGTH: 5
<212> TYPE: PRT
<213> ORGANISM: Artificial Sequence
<220> FEATURE:
<223> OTHER INFORMATION: pentapeptide component

<400> SEQUENCE: 24

Gly Val Leu Leu Val
1               5

<210> SEQ ID NO 25
<211> LENGTH: 5
<212> TYPE: PRT
<213> ORGANISM: Artificial Sequence
<220> FEATURE:
<223> OTHER INFORMATION: pentapeptide component

<400> SEQUENCE: 25

Val Val Leu Gly Leu
1               5

<210> SEQ ID NO 26
<211> LENGTH: 5
<212> TYPE: PRT
<213> ORGANISM: Artificial Sequence
<220> FEATURE:
<223> OTHER INFORMATION: pentapeptide component

<400> SEQUENCE: 26

Val Gly Leu Val Leu
1               5

<210> SEQ ID NO 27
<211> LENGTH: 5
<212> TYPE: PRT
<213> ORGANISM: Artificial Sequence
<220> FEATURE:
```

```
<223> OTHER INFORMATION: pentapeptide component

<400> SEQUENCE: 27

Gly Val Leu Val Leu
1               5

<210> SEQ ID NO 28
<211> LENGTH: 5
<212> TYPE: PRT
<213> ORGANISM: Artificial Sequence
<220> FEATURE:
<223> OTHER INFORMATION: pentapeptide component

<400> SEQUENCE: 28

Val Val Gly Leu Leu
1               5

<210> SEQ ID NO 29
<211> LENGTH: 5
<212> TYPE: PRT
<213> ORGANISM: Artificial Sequence
<220> FEATURE:
<223> OTHER INFORMATION: pentapeptide component

<400> SEQUENCE: 29

Val Gly Val Leu Leu
1               5

<210> SEQ ID NO 30
<211> LENGTH: 5
<212> TYPE: PRT
<213> ORGANISM: Artificial Sequence
<220> FEATURE:
<223> OTHER INFORMATION: pentapeptide component

<400> SEQUENCE: 30

Gly Val Val Leu Leu
1               5

<210> SEQ ID NO 31
<211> LENGTH: 7
<212> TYPE: PRT
<213> ORGANISM: Artificial Sequence
<220> FEATURE:
<223> OTHER INFORMATION: heptapeptide component

<400> SEQUENCE: 31

Leu Val Val Gly Leu Cys Lys
1               5
```